United States Patent
Wadsworth et al.

(10) Patent No.: US 7,371,242 B2
(45) Date of Patent: May 13, 2008

(54) THREE PRONGED LEVER-ACTION CASTRATION TOOL

(76) Inventors: Scott Wadsworth, 20 Dublin Gulch Rd., St. Ignatius, MT (US) 59865; Mike Wadsworth, 20 Dublin Gulch Rd., St. Ignatius, MT (US) 59865

(*) Notice: Subject to any disclaimer, the term of this patent is extended or adjusted under 35 U.S.C. 154(b) by 411 days.

(21) Appl. No.: 10/772,763

(22) Filed: Feb. 4, 2004

(65) Prior Publication Data
US 2004/0158265 A1    Aug. 12, 2004

Related U.S. Application Data

(60) Provisional application No. 60/445,757, filed on Feb. 5, 2003.

(51) Int. Cl.
*A61D 1/06* (2006.01)
*A61B 17/10* (2006.01)

(52) U.S. Cl. ............... 606/135; 606/140; 606/141

(58) Field of Classification Search ........... 606/140, 606/141, 135; 30/184, 190; 294/28; 433/3, 433/4, 15, 141; 81/486, 381, 383, 383.5, 81/302, 309
See application file for complete search history.

(56) References Cited

U.S. PATENT DOCUMENTS

| | | | |
|---|---|---|---|
| 612,569 A | 10/1898 | Moscrop | |
| 1,190,581 A * | 7/1916 | Pfeninger | ............ 294/28 |
| 1,615,125 A | 1/1927 | Lespinasse | |
| 1,885,945 A | 11/1932 | Ransy | |
| 2,125,404 A | 8/1938 | Snyder | |
| 2,384,408 A * | 9/1945 | Warren | ............ 294/28 |
| 2,487,425 A | 11/1949 | Collins | |
| 2,642,057 A | 6/1953 | Watkins | |
| 2,840,081 A * | 6/1958 | Moose | ............ 606/140 |
| 3,080,867 A | 3/1963 | Eichinger | |
| 3,547,124 A | 12/1970 | Ferguson | |
| 3,687,138 A | 8/1972 | Jarvik | |
| 3,726,278 A | 4/1973 | Scott | |
| 3,813,983 A | 6/1974 | Paul | |
| 3,983,860 A | 10/1976 | Bolton | |
| 4,156,959 A * | 6/1979 | Weisenburger | ............ 29/225 |
| 4,220,155 A | 9/1980 | Kimberling et al. | |
| 4,335,490 A | 6/1982 | Teachout | |
| 4,516,574 A | 5/1985 | Hewes, Jr. | |
| 4,569,324 A | 2/1986 | Garcia | |
| 4,572,179 A * | 2/1986 | Teitelbaum et al. | ............ 606/207 |
| 4,682,716 A | 7/1987 | Morellini | |
| 4,691,704 A | 9/1987 | Wadsworth | |
| 4,721,169 A | 1/1988 | Nagasawa et al. | |
| 4,966,600 A | 10/1990 | Songer et al. | |

(Continued)

*Primary Examiner*—Todd E. Manahan
*Assistant Examiner*—Timothy J Neal
(74) *Attorney, Agent, or Firm*—Frank J. Dykas; Derek H. Maughan; Dykas, Shaver & Nipper, LLP

(57) ABSTRACT

An easily operated castrating tool that allows placement of an improved continuous elastic band for ligation and removal of an appendage. The present invention includes a tool that allows such bands to be placed in a manner that is significantly more easy to use, and less fatiguing to the parties that utilize the device. The instant invention is also an improved elastic band which allows for better compressive ligation about a body part as well as a simple, but effective, spreading tool that allows for quicker and easier placement of the improved elastic band about a body part to be ligated.

2 Claims, 4 Drawing Sheets

U.S. PATENT DOCUMENTS

| | | |
|---|---|---|
| 4,986,369 A | 1/1991 | Fushiya et al. |
| 5,127,389 A | 7/1992 | Magnuson |
| 5,163,948 A | 11/1992 | Kummer |
| 5,188,637 A | 2/1993 | Wadsworth |
| 5,207,690 A | 5/1993 | Rohrabacher et al. |
| 5,236,434 A | 8/1993 | Callicrate |
| 5,279,276 A | 1/1994 | Nagel et al. |
| 5,282,825 A | 2/1994 | Muck et al. |
| 5,403,325 A | 4/1995 | Callicrate |
| 5,425,736 A | 6/1995 | Wadsworth |
| 5,459,905 A | 10/1995 | Voyre |
| 5,520,702 A | 5/1996 | Sauer et al. |
| 5,536,270 A | 7/1996 | Songer et al. |
| 5,681,329 A | 10/1997 | Callicrate |
| 5,855,590 A * | 1/1999 | Malecki et al. .............. 606/205 |
| 5,902,309 A * | 5/1999 | Wadsworth ................. 606/135 |
| 5,997,553 A | 12/1999 | Callicrate |
| 6,332,274 B1 * | 12/2001 | Domenge .................... 30/251 |
| 6,409,738 B2 | 6/2002 | Callicrate |

* cited by examiner

THREE PRONGED LEVER-ACTION CASTRATION TOOL

PRIORITY

This application claims the priority date of the provisional application entitled THREE PRONGED LEVER-ACTION CASTRATION TOOL filed by Scott Wadsworth and Mike Wadsworth on Feb. 5, 2003, with Ser. No. 60/445,757, the disclosure of which is incorporated herein.

BACKGROUND OF INVENTION

1. Field of Invention

This invention generally relates to ligation type castration tools, and more particularly to a lever activated stretching tool for placing a continuous elastomeric band on animals for castration or removal of other body parts.

2. Background of the Invention

In animal husbandry, it becomes necessary at times to remove body parts and appendages. Examples of such actions include removing an animal's tail, testes, or other body parts. One way that this is done is to place a ligating band at the location where the body part is to be removed. The ligating band exerts sufficient tension upon the body part so as to restrict the flow of blood into and out of the body part. As a result of this restricted blood flow, the tissue within the appendage dies and after a period of time the appendage sloughs off.

Castration by ligation has become popular because of the simplicity of the process and the benefits it provides in avoiding undesirable consequences such as microbial infection, insect invasion, excessive bleeding, and the like. Ligation type castration of younger animals has been accomplished largely by use of small preformed continuous elastic or elastomeric bands, because of the economic viability provided by allowing rapid castration processing that can be accomplished by relatively unskilled persons.

The small elastic bands are generally placed by a spreading type tool having two arms interconnected in their medial portions to allow expansion of a band carried at one end portion of the tool against its elastic bias for placement over the scrotal pouch of the animal with subsequent release. This process works well with juvenile animals that do not have a mature testicular structure of larger size, but it has not been viable with larger animals having mature testicular structure such as bovine bulls, as a small preformed elastic band that would contract to a small enough configuration to provide ligation generally cannot be expanded sufficiently, either by its nature or by use of common spreading type tools, to allow passage over the larger testicular structure of the mature animal.

In addition, most devices for spreading the elastic ligation bands have not provided the user with the ability to sufficiently spread the elastic band so as to allow the passage of testes therethrough. Therefore, the use of elastic bands for ligation has been limited by the hand strength of the person utilizing the device.

Ligation castration with continuous preformed bands is easier and less complex than the formation of ligation banding in place. It has fewer possibilities for mistakes or errors. It provides a process that requires less care and skill on the part of an operator, and generally may be more easily accomplished by unskilled workmen without historical familiarity with the process. Elongate type ligation material that is formed in place also allows parameters for tensioning and band fastening by a clip that may be varied, either accidentally or deliberately by an operator, to provide results that are not necessarily uniform or consistent and may vary sufficiently to make the process inoperative or harmful to an animal.

Continuous band ligation material has more fixed parameters determined by the nature and configuration of the banding material itself, which are more independent of an operator's activities. The continuous banding material also is generally more durable than the elongate ligation material form in place, and is less expensive and more easily handled than the elongate material. There are therefore various advantages in using preformed continuous band type elastic material for ligation castrating, when the use of such material is possible.

The nature of the ligation castration process with small preformed continuous band elastic material defines the limits of the parameters required for the elastic bands usable for such purpose, and especially their relaxed size and elastic properties. Such bands must be small enough to fulfill their ligation purpose of providing sufficient elastic force or bias after placement and fastening about the neck of the scrotal pouch to cause atrophy of the tissue outwardly of the band while yet allowing sufficient expansion upon stretching to permit placement over the scrotal pouch.

Since a continuous ligation band must allow passage of the scrotal pouch and contain the testicular structure of an animal to be castrated through the orifice it defines and because of its small size, the bands must be enlarged by stretching to allow placement. The instant invention provides a tool to simply and easily accomplish the stretching of such bands of the required nature to a size and configuration that allows placement without damage to the elastic material. The present invention describes a system made up of a continuous elastomeric band that provides a desired amount of tensioning power together with a lever action band spreading tool that provides sufficient mechanical advantage to allow the bands in the present system to be sufficiently stretched so as to allow the bands to be placed over the appendages to be removed.

The lever action spreader of the present tool provides a secondary benefit by speeding the individual castration process and allowing a single operator to accomplish a greater number of castrations in a given period of time than could be accomplished with various prior tools. In the modem practice of animal husbandry, groups of several hundred animals may be castrated over a short period of time in a continuous operation. With prior tools not providing leveraging operation, the manual force required by a workman in operating various prior castration tools was often so great, and application of that force sufficiently difficult, that the process was tiring to a workman, particularly to his hand and wrist muscles, to such an extent that the workman's physical ability became a limiting factor in the number of sequential castrations that the workman could accomplish without substantial rest. This problem could be of such extent that it might cause permanent physical damage to a workman. The instant tool resolves this problem by requiring substantially less force, and is of such nature that it is not unusually tiring or damaging to a workman, allowing continuous operation over lengthy periods of time without adverse physiological effects that may cause injury or work slow down.

The present invention also provides an advantage in that it provides mechanical advantage for spreading an elastic band by providing that the spreading of the loop occurs when the pivoting handle is pulled toward a user. This enables the greatest amount of force to be placed upon the loop by the stronger muscles of the user and allowing the band to be held in a spread position by a person with one hand. This provides significant advantages in placing and maintaining the loop in an open position for placement upon a body party to be castrated.

An additional advantage of the present invention is that the closed position occurs when the lever bar of the device is past a generally perpendicular position. This configuration allows the rubber band to be stretched, and held in a stretched position with the physical forces of the band itself holding the loop open. This provides for increased advantages to the user as they may hold the device in one hand and use the other hand for other activities.

Additional objects, advantages, and novel features of the invention will be set forth in part in the description as follows, and in part will become apparent to those skilled in the art upon examination of the following, or may be learned by practice of the invention. The objects and advantages of the invention may be realized and attained by means of the instrumentalities and combinations particularly pointed out in the appended claims.

SUMMARY OF INVENTION

The instant invention provides an easily operated castrating tool that allows placement of an improved continuous elastic band for ligation and removal of an appendage. The present invention includes a tool that allows such bands to be placed in a manner that is significantly more easy to use, and less fatiguing to the parties that utilize the device. The instant invention is also an improved elastic band which allows for better compressive ligation about a body part as well as a simple, but effective, spreading tool that allows for quicker and easier placement of the improved elastic band about a body part to be ligated.

The bands of the present invention are generally cylindrical bands with a flat top and a flat bottom. The walls of the cylinder have a thickness of about 5/16 of an inch when the rubber band is in the relaxed contracted state. These walls also have a height of about 5/16 of an inch when relaxed and an overall diameter of 11/16 of an inch. The bands define an inner opening having a circumference of about 1/4 inch. Depending upon the differing requirements of use, the dimensions may be modified, however, the overall ratios of the size of the bands should be generally maintained.

Bands having these ratios require a significant amount of force to open to a size sufficient to allow an appendage or body part, such as a scrotal pouch, to be inserted within the opening. The system of the present invention provides a device with sufficient stretching power so as to allow the bands of the present invention to be opened and for an appendage to be inserted therein.

The stretching tool of the present invention is a device made up of a pair of jaws, each having a portion configured to engage a portion of the ligating band. These jaws are also pivotally connected to a base portion, which is configured both for pivotal engagement with the jaws and for slideable engagement along a holding rail. The holding rail has a first end with a portion configured to connect and hold a portion of a ligation band and extends along a length to a handle portion which is configured to allow a user to hold and maintain the stretching tool in a desired position. The base plate is also connected to a lever. The lever has a first end pivotally connected to the base plate and extends along a length to a handle. Along the length of the lever, a bracing bar is pivotally attached. This bracing bar extends from a first end which is pivotally connected to the lever, along a length to a second end which is pivotally connected to an anchor near the handle portion of the holding rail. A pair of spacer bars is pivotally connected to the holding rail near its second end. These spacer bars extend from their connection with the holding rail along a length to a pivotal connection with a portion of the jaws.

The device is used by placing the lever in a first position. In this first position, the lever is oriented in a generally perpendicular position with regard to the holding rod. In this position, the lever pivots about the base plate and the bracing bar, causing the base plate to be moved along the holding rail toward the handle portion of the rail. As this occurs, the spacer bars pivot about their connection with the holding rail and the connection with the jaws and pull the ends of the jaws towards the portion of the holding rail which is configured to hold a ligating band. In this position, the band grasping portions of the jaws, and the holding rail, are in sufficiently close proximity so as to allow a ligating band to be placed upon the device.

Once a ligating band has been placed upon the device, the device may be moved into a second position. This is done by a user grasping the handle portion of the holding rail with one hand and the lever portion of the device with the other hand, and bringing the lever toward the holding rail. As force is applied to the lever, the lever pivots about both the pivoting connection between the base plate and the lever, as well as the connection between the bracing bar and the lever. As the lever pivots about these two points, the base plate slides along the holding rail. As the base plate moves along the holding rail, the spacer bars pivot about the connections between the spacer bars and the base plate or articulating device, and the spacer bars and the jaws.

As these spacer bars pivot, the jaws pivot about their connections with the base plate and the ends of the jaws are forced open. In as much as the ligating band is connected to these jaws, as the jaws open the ligating band is stretched and the band is prepared for placement over a body part to be ligated. The combination of distances and multiple pivot points provide significant mechanical advantage to the person utilizing the device, this allowing the bands to be opened for use with decreased amounts of effort or strength required on the part of the party utilizing the device.

Once the body part to be ligated is placed within the opening defined by the stretched band, the lever can be returned again toward the first position and the elastic band will close about the body part to be ligated. The device can then be removed, returned to a first position, loaded with another ligating band, and used again.

This system provides a method and device for ligating body parts from animals that is significantly easier to use, and more simple and efficient as compared to other methods that exist in the prior art. In addition, this invention provides a system and method for placing ligating bands, which reduces the incidence of unintended injury to animals as compared to other devices and systems known in the art.

A principal object of this invention is to provide a ligation type castration tool for larger sexually mature animals having an external scrotal pouch, and that stretches a small preformed continuous ligation band sufficiently to allow passage of a body part, such as a scrotal pouch, through the orifice defined by the stretched band. The band is then placed about the area of the interconnection of the body part to be removed, and the body structure of the animal to remove the body part and its contents.

A further object is to provide such a tool that has an expandable band holding yoke, which is collapsible so as to allow placement of a ligation band thereupon and expandable so as to stretch the band and allow expansion of the band and placement of the band upon a body part to be ligated.

A further object is to provide such a tool that has compound lever mechanisms to provide mechanical advantages to the person utilizing the device, and thereby to allow the bands to be spread sufficiently so as to allow passage of the band over a body part to be ligated.

A still further object is to provide a process for ligation castration of large mature animals having an external scrotal pouch that uses small continuous ligation bands that must be stretched to define an orifice of sufficient size to pass over the scrotal pouch of the animal.

A still further object is to provide such a tool that is of new and novel design, of rugged and durable nature, of simple and economic manufacture, and is otherwise well suited to the uses and purposes for which it is intended.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive.

DESCRIPTION OF THE PREFERRED EMBODIMENT

Figure 1:
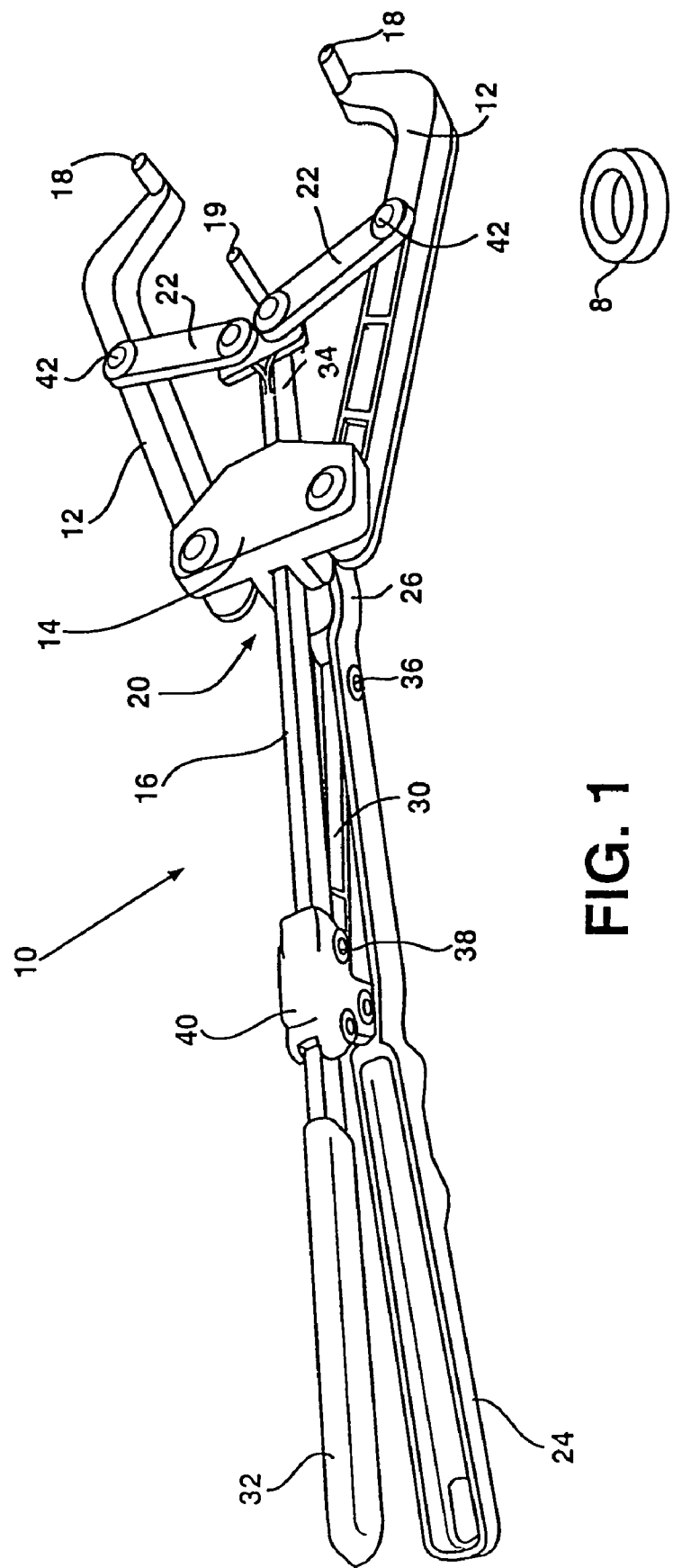
FIG. 1 is a perspective top view of the system of the present invention comprised of elastic ligating bands, and the tool for placement of these bands.

While the invention is capable of various modifications and alternative constructions, certain illustrated embodiments thereof have been shown in the drawings and will be described below in detail. It should be understood, however, that there is not intention to limit the invention to the specific form disclosed, but, on the contrary, the invention is to cover all modifications, alternative constructions, and equivalents falling within the spirit and scope of the invention as defined in the claims.

The instant invention provides an easily operated castrating tool 10 that allows placement of an improved continuous elastic band 8 for ligation and removal of an appendage. The tool of the present invention provides a tool that allows such bands 8 to be placed in a manner that is significantly more easy to use, and less fatiguing to the parties that utilize the device 10. The instant invention includes an improved elastic band 8 which allows for better compressive ligation about a body part as well as a simple, but effective, spreading tool 10 that allows for quicker and easier placement of the improved elastic band 8 about a body part to be ligated.

FIG. 1 shows a top perspective view of system of the present invention. The system of the present invention is made up of a tool 10 and a variety of bands 8 which are configured to be placed about a body part to be ligated.

The bands 8 of the present invention are generally cylindrical bands having a flat top and a flat bottom. The walls of the cylinder have a thickness of about $5/16$ of an inch when the band is in the relaxed contracted state. These walls also have a height of about $5/16$ of an inch when relaxed and an overall diameter of $11/16$ of an inch. The bands define an inner opening having a circumference of about ¼ inch. Depending upon the differing requirements of use, the dimensions may be modified, however, the overall ratios of the size of the bands 8 should be generally maintained. These bands also have additional features in that they are coated with an antiseptic property, such as an antiseptic powder, which further fights against infection and other negative possible side effects from the ligation procedure.

Bands 8 having these ratios require a significant amount of force to open to a size sufficient to allow an appendage or body part, such as a scrotal pouch, to be inserted within the opening. The system of the present invention provides a device with sufficient stretching power so as to allow the bands 8 of the present invention to be opened and for an appendage to be inserted therein.

The stretching tool 10 of the present invention is a device made up of a pair of jaws 12, each having a portion 18 configured to engage a portion of the ligating band 8. These jaws 12 are also pivotally connected to a base portion 14, which is configured both for pivotable engagement with the jaws 12 and for slideable engagement along a holding rail 16. This base portion 14 is a part of an articulating device 20 which is utilized that is used in conjunction with a lever 24 to move the spacer bars 22 to spread the band 8. The holding rail 16 has a first end 34 with a portion 19 configured to connect and hold a portion of a ligation band 8, and extends along a length to a handle portion 32 which is configured to allow a user to hold and maintain the stretching tool 10 in a desired position. The base plate 14 is also connected to a lever 24. The lever 24 has a first end 26, which is pivotally connected to the base plate 14 and extends along a length to a handle 32. Along the length of the lever 24 a bracing bar or arm 30 is pivotally attached. This bracing bar 30 extends from a first end 36, which is pivotally connected to the lever 24, along a length to a second end 38, which is pivotally connected to an anchor 40 positioned near the handle portion 32 of the holding rail 16. A pair of spacer bars 22 is pivotally connected to the holding rail 16 near its second end 34. These spacer bars 22 extend from their connection with the holding rail 16 along a length to a pivotal connection 42 with a portion of the jaws 12.

Figure 2:
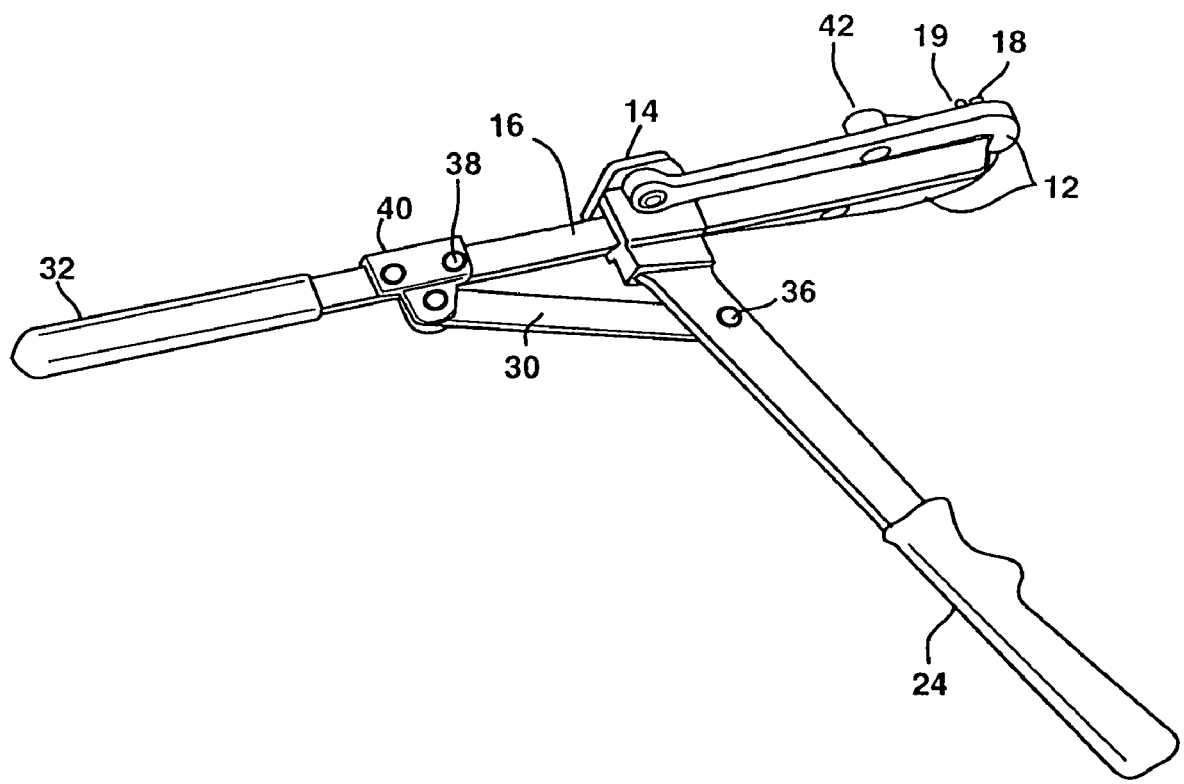
FIG. 2 is a perspective bottom view of the tool of the present invention in a first position.

FIG. 2. shows the tool 10 of the present invention in a first position. In this first position, the lever 24 is oriented in a generally perpendicular position with regard to the holding rod 16. In this position, the lever 24 pivots about the base plate 14 and the bracing bar 30, causing the base plate 14 to be moved along the holding rail 16 toward the handle 32 portion of the rail 16. As this occurs, the spacer bars 22 pivot about their connection with the holding rail 16 and the connection with the jaws 12 and pull the ends of the jaws 18 towards the portion of the holding rail 19, which is configured to hold a ligating band 8. In this position, the band grasping portions of the jaws 18 and the holding rail 19 are in sufficiently close proximity so as to allow a ligating band 8 to be placed upon the device 10.

Figure 3:
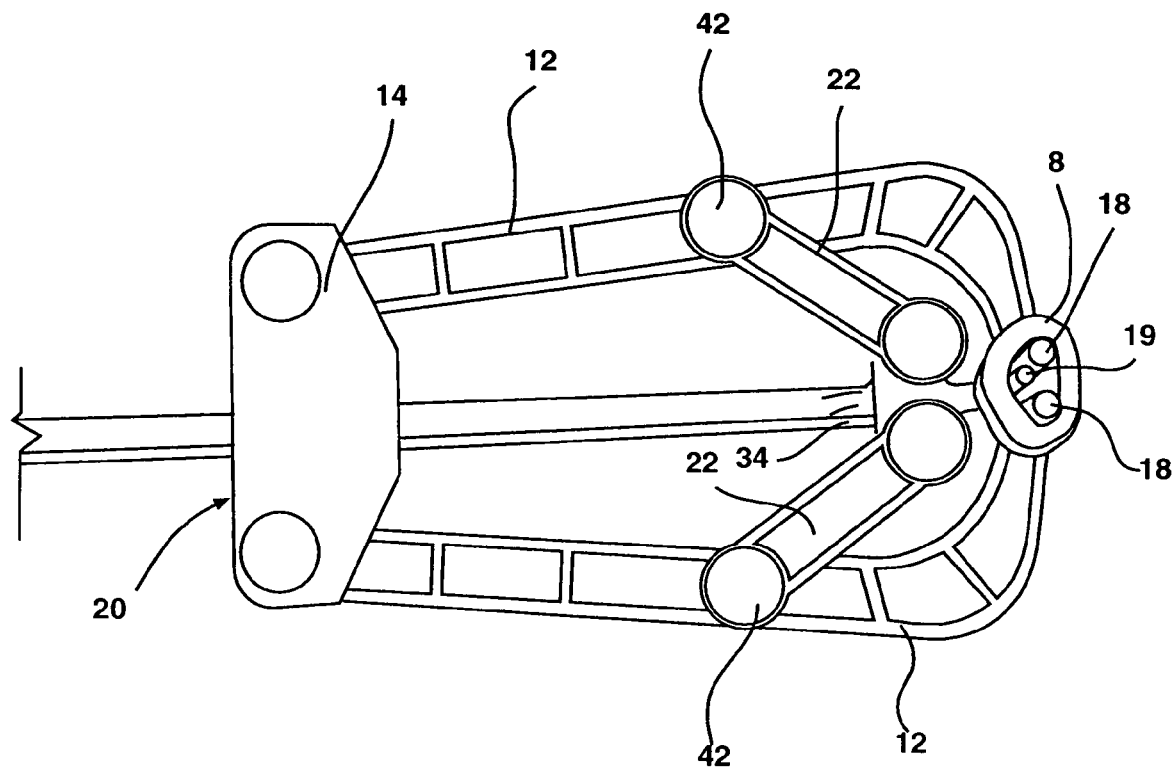
FIG. 3 is a detailed top view of the tool shown in FIG. 2, showing placement of a ligation band thereupon.

A detailed top view of the positioning of the jaws and the ligating band placed upon the tool is shown in FIG. 3.

While in FIG. 2 the position of the holding rail 16 and the lever 24 is described as being generally perpendicular, in the preferred embodiment the position of the lever 24 with regard to the holding rail 16 bar is about fifteen degrees past a completely perpendicular orientation. This feature provides a variety of benefits. First, this position assists in providing mechanical advantage sufficient to produce an initial force sufficient to stretch the band 8. By allowing a longer path of travel for the lever 24, the lever 24 is able to pivot about the connection between the bracing bar 30 and the lever 24. This creates a force which is then transferred and sent to the connection between the lever 24 and the base plate 14. The lengths of the spacing arms 22 and the pivots involved provide increases in force placed upon the band and allow the band 8 to stretch all without a significant amount of work on the part of the person utilizing the device 10.

Figure 4:
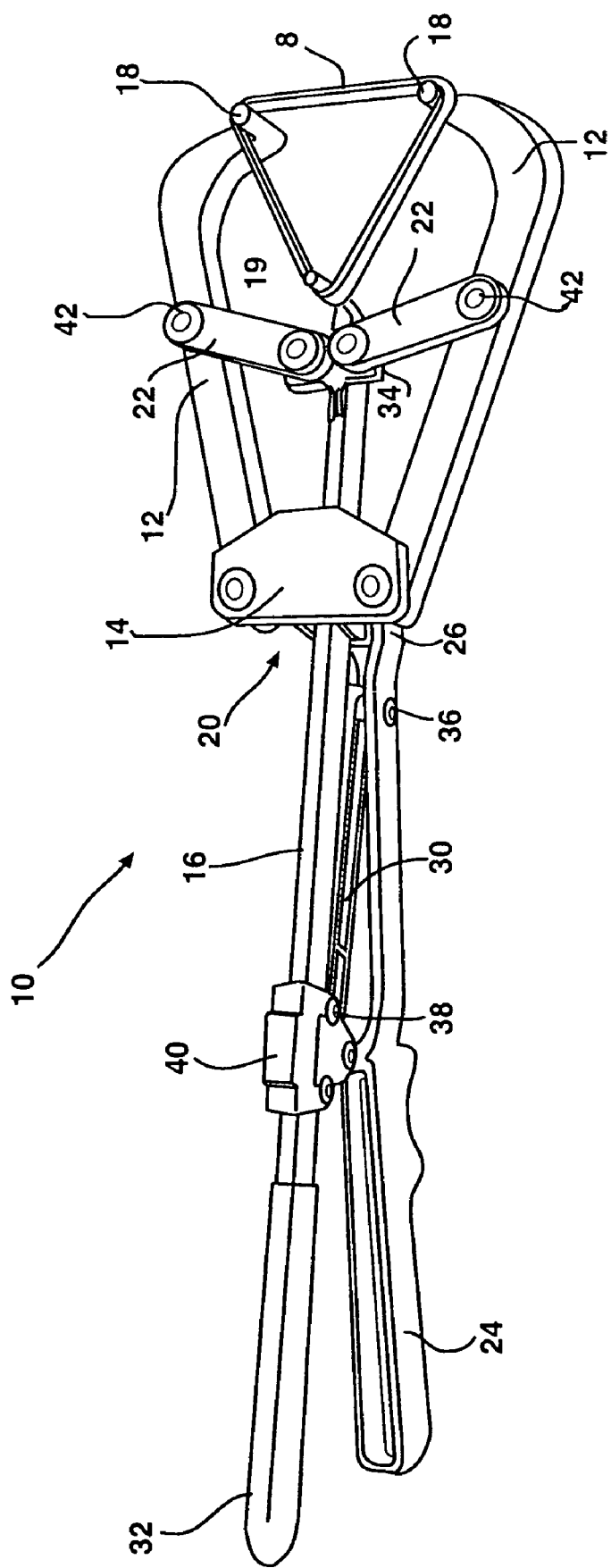
FIG. 4 is a top perspective view of the invention showing a ligation band placed and stretched thereupon.

This embodiment of the invention in an open position with a stretched band as shown in FIG. 4.

Once a ligating band 8 has been placed upon the device 10, the device 10 may be moved into a second position. Moving the device 10 into the second position is done by a user grasping the handle 32 portion of the holding rail 16 with one hand and the lever 24 portion of the device with the other hand and bringing the lever 24 toward the holding rail 16. As force is applied to the lever 24, the lever 24 pivots about both the pivoting connection between the base plate 14 and the lever 24, as well as the connection between the bracing bar 30 and the lever 24. As the lever 24 pivots about these two points, the base plate 14 slides along the holding rail 16. As the base plate 14 moves along the holding rail 16, the spacer bars 22 pivot about the connections between the spacer bars 22 and the holding rail 16, and the spacer bars 22 and the jaws 12. As these spacer bars 22 pivot, the jaws 12 pivot about their connections with the base plate 14 and the ends of the jaws 12 are forced open. In as much as the ligating band 8 is connected to these jaws 12, as the jaws 12 open the ligating band 8 is stretched and the band 8 is prepared for placement over a body part to be ligated.

The combination of distances and multiple pivot points provide significant mechanical advantage to the person utilizing the device, this allowing the bands 8 to be opened for use with decreased amounts of effort or strength required on the part of the party utilizing the device. An additional advantage of the present invention is that the device 10 can be maintained in an open position with one hand.

In order to move the device into the open position, the lever 24 must be moved from the past perpendicular position shown in FIG. 2 toward the handle 32 that is positioned upon the holding rod 16 to the position shown in FIG. 4. At this position, the band 8 compresses the ends of the jaws 12 toward each other. This compressive force causes the base plate 14 to be moved toward the first end 34 of the holding rod 16. This force then causes the lever 24 to pivot about the connection between the lever and the base plate 14 and the connection between the bracing arm 30 and the lever 24. This causes the lever 24 to be moved toward the handle 32 of the holding rod 16 thus locking the device in the open position shown in FIG. 1 and FIG. 4. Thus the present invention utilizes the naturally compressive forces of the elastic band to hold the stretching device in an open position and allows a user to hold a stretched device in an open position with just one hand and frees up the other hand for use in other activities.

Once the body part to be ligated is placed within the opening defined by the stretched band 8, the lever 24 can be returned again toward the first position, and the elastic band 8 will close about the body part to be ligated. The device can then be removed, returned to a first position, loaded with another ligating band 8, and used again.

This system provides a method and device for ligating body parts from animals that is significantly easier to use, more simple and efficient as compared to other methods which exist in the prior art. In addition, this invention provides a system and method for placing ligating bands which reduces the incidence of unintended injury to animals as compared to other devices and systems known in the art.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

We claim:

1. A device for stretching an endless loop of resiliently stretchable material for use in removing body parts by constricting blood flow, said device comprised of a holding rail
    a pair of jaws configured to engage a portion of said endless loop, said jaws further pivotally connected to a base portion, said base portion configured for slideable engagement along said holding rail in a first plane of movement, said holding rail also having a portion configured to engage a portion of said endless loop and a portion connected to a grasping handle, and an articulating device configured to move said base portion along said holding rail so as to manipulate said jaws, so as to engage and stretch said endless loop, said articulating device moving in a second plane generally perpendicular to said first plane of movement, said articulating device including a pair of spacer bars pivotally connected to said jaws, and pivotally connected to a portion of said holding rail, said spacer bars configured to alternatively open and close said jaws when said base portion is alternatively moved along said holding rail.

2. A device for stretching an endless loop of resiliently stretchable material for use in removing body parts by constricting blood flow, said device comprised of a holding rail
    a pair of jaws configured to engage a portion of said endless loop, said jaws further pivotally connected to a base portion, said base portion configured for slideable engagement along said holding rail in a first plane of movement, said holding rail also having a portion configured to engage a portion of said endless loop and a portion connected to a grasping handle, and an articulating device configured to move said base portion along said holding rail so as to manipulate said jaws, so as to engage and stretch said endless loop, said articulating device moving in a second plane generally perpendicular to said first plane of movement, wherein said holding rail is pivotally connected to a pair of spacer bars, said spacer bars also pivotally connected to said jaws, whereby advancing said base portion along said holding rail causes said jaws to open a distance determined by the lengths of said spacer bars.

\* \* \* \* \*